US00PP19919P2

(12) United States Plant Patent
Bradford

(10) Patent No.: US PP19,919 P2
(45) Date of Patent: Apr. 14, 2009

(54) PEACH TREE NAMED 'PEARL PRINCESS V'

(50) Latin Name: *Prunus persica*
Varietal Denomination: Pearl Princess V

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/003,404

(22) Filed: Dec. 26, 2007

(51) Int. Cl.
*A01H 5/00* (2006.01)

(52) U.S. Cl. ..... Plt./196
(58) Field of Classification Search ..... Plt./196
See application file for complete search history.

(56) References Cited

U.S. PATENT DOCUMENTS

| | | | |
|---|---|---|---|
| PP9,960 | P | 7/1997 | Bradford |
| PP12,570 | P2 | 4/2002 | Bradford |
| PP12,974 | P2 | 9/2002 | Bradford |

*Primary Examiner*—Annette H Para
*Assistant Examiner*—June Hwu

(57) ABSTRACT

The present invention relates to a new and distinct variety of peach tree, *Prunus persica,* broadly characterized by a medium size, vigorous, hardy, self-fertile, productive and regular bearing tree. The variety blooms during the mid season and requires about 500 chilling hours. The fruit matures under the ecological conditions described in early June, with first picking on Jun. 19, 2007. The fruit is uniformly large in size, a tasty balance of acid and sugar in flavor, globose in shape, freestone in type, firm and melting in texture, white in flesh color, and mostly red in skin color.

1 Drawing Sheet

Botanical classification: *Prunus persica.*
Variety denomination: 'Pearl Princess V'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of peach tree, which has been denominated varietally as 'Pearl Princess V'.

The present variety was hybridized by me in 2000 as a first generation cross using 'Grand Pearl' (U.S. Plant Pat. No. 9,960) nectarine as the selected seed parent and 'Snow Princess' (U.S. Plant Pat. No. 12,570) peach as the selected pollen parent. The fruit of this cross was gathered that summer, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2004 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent 'Grand Pearl' nectarine by producing fruit that is white in flesh color, mostly red in skin color, and very sweet and sub-acidic in taste, but is quite distinguished therefrom by requiring less chilling hours, by being a peach instead of nectarine, and by producing fruit that matures about three weeks earlier.

The present variety is similar to its pollen parent, 'Snow Princess' (U.S. Plant Pat. No. 12,570) peach by producing peaches that are large, firm, freestone in type, white in flesh color, and mostly red in skin color, but is distinguished therefrom by producing fruit that is sweeter in flavor and that matures about thirty days earlier.

The present variety is more similar to 'Ice Princess' (U.S. Plant Pat. No. 12,974) peach by producing peaches that are firm in texture, freestone in type, white in flesh color, and mostly red in skin color, but is distinguished therefrom by producing fruit that is larger in size, that matures about sever days earlier, and that is a tasty balance of acid and sugar rather than sub-acidic in flavor.

SUMMARY OF VARIETY

In summary, the present variety is characterized by a medium size, vigorous, hardy, self-fertile, productive and regular bearing tree. The variety blooms during the mid season and requires about 500 chilling hours. The fruit matures under the ecological conditions described in early June, with first picking on Jun. 19, 2007. The fruit is uniformly large in size, a tasty balance of acid and sugar in flavor, globose in shape, freestone in type, firm and melting in texture, white in flesh color, and mostly red in skin color.

DRAWING

The accompanying photograph consists of four whole fruits positioned to display the characteristics of the skin color and form, one divided fruit to reveal the flesh and stone, two insets to reveal buds and a blossom, typical leaves, and a tip shoot.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 22, 2007, on the original tree during its seventh growing season. The blossom and flower descriptions were made the previous blooming season. All major color code designations are by reference to the Inter-Society Color Council, National Bureau of Standards. Common color names are also used occasionally.

Parentage

Seed parent: 'Grand Pearl' (U.S. Plant Pat. No. 9,960) nectarine.

Pollen parent: 'Snow Princess' (U.S. Plant Pat. No. 12,570) peach.

Tree

Size: Medium, reaching and maintaining a height of 10' [3.05 m.] and a spread of 7' [2.13 m.] after seven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Approximate chilling requirement: 500 hours.

Trunk:

*Size.*—Slender, reaching a maximum diameter of 3¼" [83 mm.] after the seventh growing season.

*Texture.*—Shaggy.

*Bark color.*—A Light grayish brown [60. l.gy.Br] and Grayish brown [61. gy.Br] variegation with Moderate orange yellow [71. m.OY] crevices present.

*Lenticels.*—Approximate Number Per Square Inch: 10. Color: Moderate orange yellow [71. m.OY]. Average Size: 3/16" [4.8 mm.]. Shape: Eye-shaped, elongated.

Branches:

*Size.*—Diameter of limb is 2¼" [57.2 mm.] measured 12" above the crotch, 1¼" [31.8 mm.] measured 12" above the first fork.

*Texture.*—Smooth on first and second year wood, increasing roughness with age.

*Color.*—1st Year Wood Topside: Grayish red [19. gyR]. 1st Year Wood Underside: Brilliant yellow green [116. brill.YG]. Older Wood: Deep yellowish brown [75. deep yBr].

*Lenticels.*—Number Per Square Inch: More than 60 on second year wood. Color: Light yellowish brown [76. l.yBr]. Average size: 1/32" [0.8 mm.] on second year wood. Shape: Rectangular, elongated.

Leaves:

*Size.*—Medium. Average Length: 5¾" [146 mm.]. Average Width: 1½" [38 mm.].

*Arrangement.*—Alternate.

*Thickness.*—Medium.

*Form.*—Elliptical.

*Apex.*—Acuminate.

*Base.*—Acute, with an average base angle of 70 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: 7/16" [11.1 mm.]. Average Thickness: 1/16" [1.6 mm.]. Color: Very yellow green [115. v.YG].

*Stipules.*—Number: Usually 2 per leaf, up to 6 per growing tip. Average Length: ¼" [6.4 mm.]. Color: Strong yellow green [117. s.YG] becoming Moderate reddish brown [43. m.rBr] with maturity.

*Glands.*—Number: 2 to 4 per leaf. Position: Alternately positioned on petiole and base of blade. Size: Medium. Form: Reniform. Color: Brilliant yellow green [116. brill.YG] becoming Moderate reddish brown [74. m.rBr] with age.

*Leaf buds.*—Pointed, medium in size.

Flower buds:

*Hardiness.*—Hardy, with respect to central California winters.

*Diameter.*—Typically ⅜" [9.5 mm.] 1 week before bloom.

*Length.*—Typically 11/16" [17.5 mm.] 1 week before bloom.

*Form.*—Not appressed.

*Surface.*—Pubescent.

*Tip color.*—Moderate purplish pink [250. m.pPk].

Flowers: Perfect, complete, perigynous, usually a single pistil, typically thirty or more stamens, five sepal and petal locations alternately positioned.

*Type.*—Showy, large.

*Average flower diameter.*—2 3/16" [55.6 mm.].

*Number of petals.*—Some with only five, more than half have extra petal fragments or are full double blossoms with ten petals.

*Petal shape.*—Circular to oval.

*Petal margin.*—Entire, very wavy, occasional notches.

*Average petal diameter.*—⅞" [22.2 mm.].

*Average petal length.*—15/16" [23.8 mm.].

*Petal apex.*—Rounded.

*Petal base.*—Rounded to somewhat truncate.

*Petal color.*—Pale pink [7. p.Pk] toward the apex, Light purplish pink [249. l.pPk] toward the base on both sides.

*Anther color.*—Deep orange [51. deep O] over a Light yellow [86. l.Y] center at bloom onset.

*Stigma color.*—Pale yellow green [121. p.YG].

*Sepal color.*—Dark purplish red [259. d.pR] on the outer surface.

*Sepal length.*—¼" [6.4 mm.].

*Sepal width.*—3/16" [4.8 mm.].

*Sepal apex.*—Rounded to elliptical to match the sepal length and width.

*Sepal margin.*—Fairly smooth.

*Average pistil length.*—5/8" [15.9 mm.].
*Average stamen length.*—9/16" [14.3 mm.].
*Fragrance.*—Moderate.
*Blooming period.*—Medium, six days after 'Snow Princess' (U.S. Plant Pat. No. 12,570) peach.
*Onset of bloom.*—One percent on Feb. 27, 2007.
*Date of full bloom.*—Mar. 8, 2007.
*Duration of bloom.*—One to two weeks, dependent on ambient temperature.
*Number per cluster.*—1 to 3 with single flowers most common.

FRUIT

Maturity when described: Firm ripe, Jun. 22, 2007.
Date of first picking: Jun. 19, 2007.
Date of last picking: Jun. 29, 2007.
Size: Uniform, large.
*Average diameter axially.*—2 15/16" [74.8 mm.].
*Average diameter across suture plane.*—3 3/16" [80.8 mm.].
*Average diameter across cheek plane.*—3 5/16" [84.2 mm.].
*Typical height.*—11.4 ounces [323 grams].
Form: Uniform, symmetrical.
*Longitudinal section form.*—Round to elliptical.
*Axial view.*—Round.
Suture: Extends from the base, along the side, to just beyond the pistil point.
*Near the base.*—A shallow, sharp groove.
*Along the side.*—A shallow trough.
*Near the apex.*—A shallow groove.
Ventral surface: Rounded, lightly lipped throughout.
Lips: Slightly unequal.
Cavity: Flaring, elongated in the suture plane, suture showing on both sides, Pale greenish yellow [104. p.gY] stem markings typical.
*Depth.*—7/16" [11.1 mm.].
*Breadth.*—1 3/8" [34.9 mm.].
Base: Rounded to somewhat truncate.
Apex: Rounded.
Pistil point: Apical, very short in length, usually depressed within the suture.
Stem: Medium.
*Average length.*—7/16" [11.1 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—Very slight.
*Color.*—Very deep red [14. v.deep R] smoothly blending into Moderate red [15. m.R] with an occasional Pale greenish yellow [104. p.gY] area where sun protected.
*Down.*—Moderate, does not roll up when rubbed.
Flesh:
*Color.*—Yellowish white [92. yWhite] acquiring some Deep pink [3. deep Pk] streaking toward stone with maturity.
*Surface of pit cavity.*—Covered with Moderate pink [5. m.Pk] fibers.
*Amygdalin.*—Scarce.
*Juice.*—Moderate, rich.
*Texture.*—Firm, crisp.
*Fibers.*—Abundant, fine, tender.
*Ripens.*—Earlier toward the apex.
*Flavor.*—A tasty balance of acid and sugar, typically 16 to 20 brix.
*Aroma.*—Moderate.
*Eating quality.*—Excellent.

STONE

Type: Freestone.
Form: Oval.
Hilum: Narrow, oblong.
Base: Rounded.
Apex: Acute with an average angle of 75 degrees.
Sides: Equal.
Surface: Regularly furrowed toward the apex and ventral edge, pitted toward the base.
Ridges: Jagged.
External color: Moderate-yellowish brown [77. m.yBr] retaining some Moderate red [15. m.R] coloration from the flesh.
Pit wall color when cracked: Light yellowish brown [76. l.yBr].
Cavity surface color: Strong yellowish brown [74. s.yBr].
Average pit wall thickness: 1/4" [6.4 mm.].
Average width: 1 1/16" [27.0 m.].
Average length: 1 1/2" [38.1 mm.].
Average breadth: 13/16" [20.6 mm.].
Tendency to split: Very slight.
Kernel:
*Form.*—Oval.
*Skin color.*—Light yellow [86. l.Y] when first removed.
*Pellicle color.*—Grayish yellow [90. gy.Y].
*Vein color.*—Moderate yellow [87. m.Y].
*Taste.*—Bitter.
*Viable.*—Yes.
*Average width.*—7/16" [11.1 mm.].
*Average length.*—13/16" [20.6 mm.].
*Amygdalin.*—Abundant.

Use

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is similar to 'Ice Princess' (U.S. Plant Pat. No. 12,974) peach by producing peaches that are firm in texture, freestone in type, white in flesh color, and mostly red in skin color, but is distinguished therefrom by producing fruit that is larger in size, that matures about several days earlier, and that is a tasty balance of acid and sugar rather than sub-acidic in flavor.

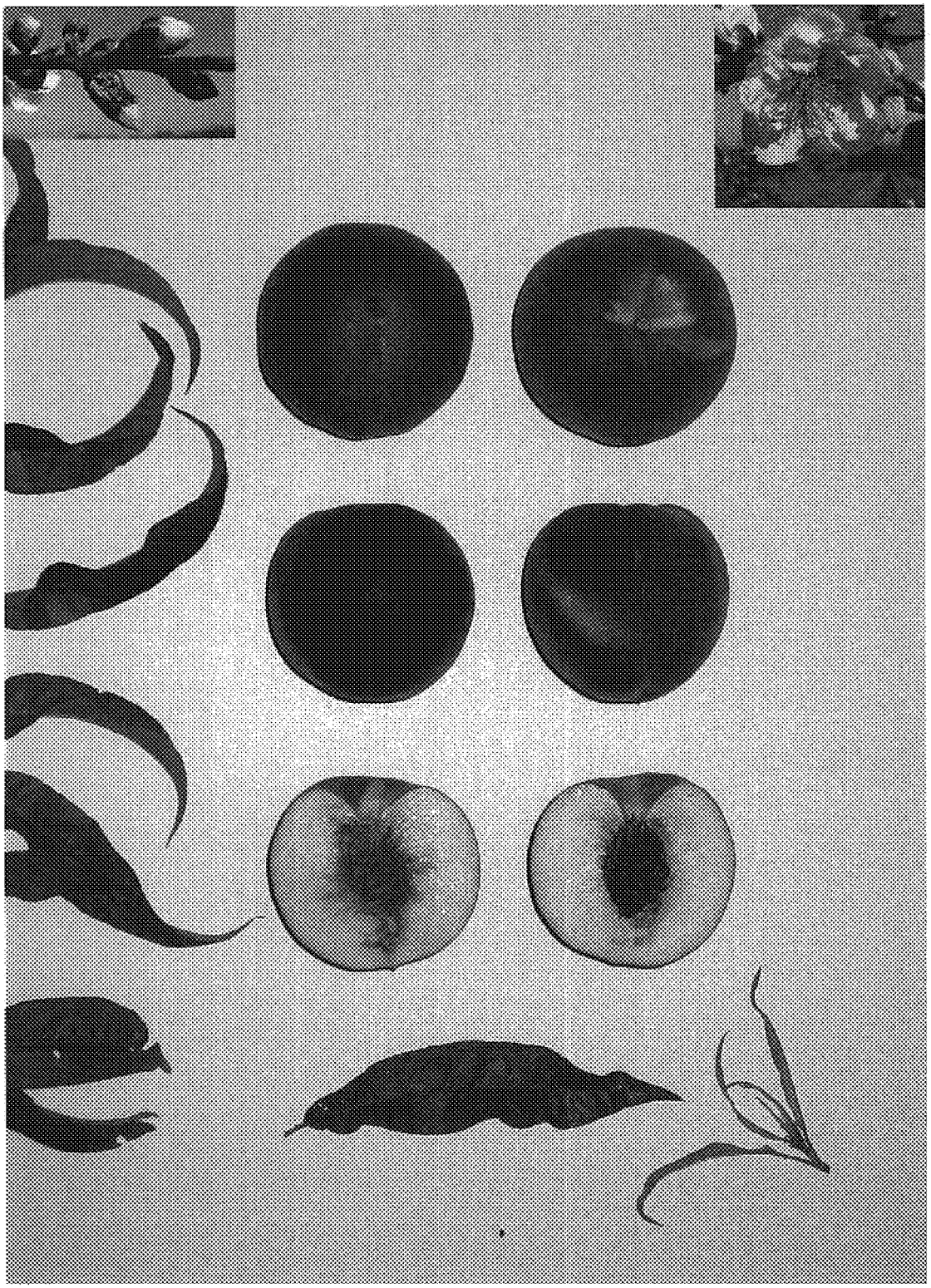

* * * * *